United States Patent [19]

Aoki et al.

[11] Patent Number: 5,043,425
[45] Date of Patent: Aug. 27, 1991

[54] THROMBIN-BINDING PROTEIN SUBSTANCE AND PROCESS FOR PREPARING THE SAME

[75] Inventors: Nobuo Aoki, Tokyo; Shigeru Kimura, Higashiyamato; Masami Shiratsuchi, Musashimurayama, all of Japan

[73] Assignee: Kowa Co., Ltd., Nagoya, Japan

[21] Appl. No.: 394,715

[22] Filed: Aug. 16, 1989

[30] Foreign Application Priority Data

Aug. 29, 1988 [JP] Japan .................................. 63-214139
Mar. 8, 1989 [JP] Japan .................................. 1-202027
May 10, 1989 [JP] Japan .................................. 1-116471

[51] Int. Cl.$^5$ .......................... C07K 3/20; C07K 3/28; C07K 15/06; C07K 15/14
[52] U.S. Cl. .................................. 530/350; 530/413; 530/395; 530/834; 514/8; 514/21; 435/70.1; 435/70.3
[58] Field of Search ............... 530/395, 350, 413, 804; 514/8, 21; 435/70.1, 70.3

[56] References Cited

U.S. PATENT DOCUMENTS

4,748,156  5/1988  Aoki et al. ............................. 514/21

FOREIGN PATENT DOCUMENTS

0155852   9/1985  European Pat. Off. ..
0239644  10/1987  European Pat. Off. ..
0253331   1/1988  European Pat. Off. ..
63-301791 12/1988  Japan .
64-6219    1/1989  Japan .
8700050    1/1987  World Int. Prop. O. ..

OTHER PUBLICATIONS

The Journal of Biological Chemistry, vol. 259, No. 19, Oct. 1984, H. H. Salem et al, pp. 12246-12251.
Thrombosis Research, vol. 37, 1985, pp. 353-364, S. Kurosaw et al.
Biological Abstracts, vol. 81, 1986, Abstract No. 91313, H. Ishii et al.
The Embo Journal, vol. 6, No. 7, 1987, pp. 1891-1897, K. Suzuki.
The Journal of Biological Chemistry, 1984, pp. 12246-12251, vol. 259, No. 19, Hatem H. Salem, et al., "Isolation and Characterization of Thrombomodulin from Human Placenta".
J. Clin. Invest., vol. 76, Dec. 1985, pp. 2178-2181, Hidemi Ishii et al., "Thrombomodulin is Present in Human Plasma and Urine".

*Primary Examiner*—Howard E. Schain
*Attorney, Agent, or Firm*—Oblon, Spivak, McClelland, Maier & Neustadt

[57] ABSTRACT

Novel thrombin-binding substances (A) and (B) are disclosed. The thrombin-binding substances have the following characteristics:
(a) molecular weight:
  Thrombin-binding substance (A):
    90,000-92,000 under reduced conditions
    55,000-58,000 under unreduced conditions
  Thrombin-binding substance (B):
    98,000-105,000 under reduced conditions
    60,000-65,000 under unreduced conditions
(b) isoelectric point:
  Thrombin-binding substance (A): pH 6.0-6.8
  Thrombin-binding substance (B): pH 5.8-6.5
(c) affinity: strong affinity to thrombin
(d) activity:
  (1) capable of promoting the thrombin catalyzed activation of protein C
  (2) prolongs clotting time; and
(e) stability: stable to denaturing agents (sodium dodecylsulfate and urea).

The thrombin-binding substances are useful as a medicine for curing thrombosis.

7 Claims, No Drawings

THROMBIN-BINDING PROTEIN SUBSTANCE AND PROCESS FOR PREPARING THE SAME

BACKGROUND OF THE INVENTION

1. Field of the Invention

This invention relates to a novel thrombin-binding substance, and, more particularly, to a thrombin-binding substance useful as a medicine, especially a medicine for curing thrombosis and the like, involving anticoagulation and fibrinolytic systems which control blood coagulation, and a process for the preparation of the thrombin-binding substance.

2. Description of the Background

A great deal of work have been done regarding the role that thrombin plays as a proteolytic enzyme in the control mechanism of blood coagulation and the mechanism of blood coagulation has been elucidated for the most part.

According to a publication it was reported that thrombin activated Protein C which is said to act on the fibrinolytic and anticoagulant systems. The publication also reports that there is a certain substance in extracts of rabbit lung tissue which functions as a coenzyme for the activation mechanism. Such a substance was named thrombomodulin [N. L. Esmon et al, *J. Biological Chemistry*, 257, (2), 859-864 (1982)].

N. Aoki, one of the present inventors, and others have reported human thrombomodulin separated from human placenta and having characteristics similar to the thrombomodulin reported by *J. Biological Chemistry*, with a molecular weight of about 71,000 under unreduced conditions [*Thromb. Res.*, 37, 353-364 (1985)].

Furthermore, I. Maruyama et al reported that the comparison of activities of human thrombomodulin separated from human placenta with a molecular weight of about 71,000 (under unreduced conditions) and those of the above-mentioned rabbit thrombomodulin revealed that they had identical activities [*J. Clin. Invest.*, 75, 987-991 (1985)].

It has also been reported by H. Ishii et al that human plasma and urine contain substances having the same activities as thrombomodulin and the molecular weights of such substances in plasma are 63,000 and 54,000 [*J. Clin. Invest.*, 76, 2178-2181 (1985)].

The present inventors had discovered in human urine two types of thrombin-binding substances which are different from the above-mentioned substances and having smaller molecular weights, i.e., about 39,000 and 31,000 under unreduced conditions, and filed a patent application on these substances (Japanese Patent Laid-open No. 146898/1988).

The inventors have continued further extensive studies in order to develop an advantageous process for the production, isolation, and purification of human thrombomodulin, and as a result separated from human urine two types of thrombin-binding substances [hereinafter defined as thrombin-binding substances (A) and (B)] which are different from above-mentioned previously discovered substances. The inventors confirmed that the two thrombin-binding substances are novel compounds.

The present inventors conducted further studies in order to develop an industrially advantageous process for producing and isolating these thrombin-binding substances. As a result, the inventors discovered that the same thrombin-binding substances found in urine are present in a culture broth of cells derived from human tissues and that the target substances can be separated add collected from the culture broth using simple procedures. Such findings have led to the completion of the present invention.

SUMMARY OF THE INVENTION

Accordingly, an object of the present invention is to provide thrombin-binding substances (A) and (B) having the following characteristics:
(a) molecular weight:
  Thrombin-binding substance (A):
    90,000-92,000 under reduced conditions
    55,000-58,000 under unreduced conditions
  Thrombin-binding substance (B):
    98,000-105,000 under reduced conditions
    60,000-65,000 under unreduced conditions
(b) isoelectric point:
  Thrombin-binding substance (A): pH 6.0-6.8
  Thrombin-binding substance (B): pH 5.8-6.5
(c) affinity: strong affinity to thrombin
(d) activity:
  (1) capable of promoting the thrombin catalyzed activation of protein C
  (2) prolongs clotting time; and
(e) stability: stable to denaturing agents (sodium dodecylsulfate and urea).

Another object of the present invention is to provide a process for preparing said thrombin-binding substances which comprises: treating human urine with calcium ion, and separating and purifying a thrombin-binding substance by immunoadsorption column chromatography using a monoclonal antibody, which is capable of recognizing structural changes in the thrombin-binding substance by calcium ion, and by a molecular weight fractionation method.

Still another object of the present invention is to provide a process for preparing said thrombin-binding substances which comprises: culturing cells derived from human tissues, and separating and purifying the thrombin-binding substance from the culture broth.

Other objects, features and advantages of the invention will hereinafter become more readily apparent from the following description.

DETAILED DESCRIPTION OF THE INVENTION AND PREFERRED EMBODIMENTS

The thrombin-binding substances of the present invention is useful as a fibrinolytic accelerator or as an anticoagulant since they combine with thrombin and specifically activate protein C and prolong the blood clotting time.

The thrombin-binding substances of this invention can be prepared, for example, by the following methods:

METHOD (1)

Treating human urine with calcium ion, and separating and purifying the thrombin-binding substances by immunoadsorption column chromatography using a monoclonal antibody which is capable of recognizing structural changes in the thrombin-binding substances caused by the calcium ion, followed by a molecular weight fractionation.

METHOD (2)

Culturing cells derived from human tissues and performing the same separation and purification procedures as Method (1) mentioned above.

In the above first method, fresh human urine or a human urine concentrate is used. They may be pretreated by one or more methods selected from ion-exchange chromatography, gel filtration, affinity chromatography using a thrombin-bound carrier, and the like.

When ion-exchange chromatography is used for the pretreatment, it is preferable that urine of which pH is adjusted to 8-12 is contacted with DEAE-Sephadex A-50 (trade name, product of Pharmacia AB), DEAE-TOYOPEARL 650C, 650M, or 650S (trade name, product of Toyo Soda Mfg. Co., Ltd.), QAE-Sephadex A-50 (trade name, product of Pharmacia AB), or the like to adsorb the target substances, and washed with a buffer solution containing a salt, e.g. sodium chloride, at a low concentration, followed by elution with the same buffer solution with a higher salt concentration. Gel filtration is carried out using Sephadex G 150 (trade name, product of Pharmacia AB), Ultrogel AcA 34 (trade name, product of LKS Co.), or the like as a carrier. Affinity column chromatography can be carried out using a thrombin-bound carrier in which thrombin is inactivated, for example, with diisopropylfluorophosphate, and bound on an insoluble carrier, for example, agarose gel, sepharose gel, dextran gel, polyvinyl gel, or the like.

Treatment of urine with calcium ion is performed by adding a calcium compound such as calcium chloride, calcium carbonate, calcium hydroxide, or the like either immediately before immuneadsorption column chromatography or during the pretreatment. In general, the addition of these compounds in an amount to bring the calcium ion concentration to 2-10 mM causes thrombin-binding substances having a calcium-binding site to selectively combine with calcium and to change their structure.

The monoclonal antibody capable of specifically recognizing such structural changes can be prepared, for example, by fusing mouse spleen cells, which have been immunized with the above-mentioned thrombin-binding substances extracted from human placentae and having a molecular weight of about 71,000, with mouse myeloma cells P3-Ag8-γ, selecting antibody producing hybridomas, then selecting hybridomas which do not immunologically react with the thrombin-binding substances in the presence of EDTA, i.e., hybridomas which produce an antibody which is capable of recognizing such structural changes, followed by conventionally known methods (Japanese Patent Laid-open No. 45398/1989). It is desirable to use as an immunoadsorbent a monoclonal antibody bound carrier in which a monoclonal antibody for the thrombin-binding substances is bound on an insoluble carrier such as dextran gel, agarose gel, polyvinyl gel, or the like. Elution by immune adsorption column chromatography can be carried out using, for example, a buffer solution containing EDTA.

High performance liquid chromatography using ion-exchange resin or electrophoresis can be used for the molecular weight fractionation. An anion-exchange resin such as TSK gel, e.g. DEAE-5PW, DEAE-2SW, or DEAE-3SW, (trade names, product of Toyo Soda Mfg. Co., Ltd.), Mono Q HR5/5 (trade name, product of Pharmacia AB), or the like is preferable as an ion-exchange resin for high performance liquid chromatography. Conventional methods, for example, the Laemmli's method using SDS-polyacrylamide gel [*Nature*, 227, 680–685 (1970)] can be used as a method for electrophoresis.

Cells which can be used in the present invention may be any cells derived from human and are capable of producing the thrombin-binding substances of the present invention. Such cells include, for example, cells derived from kidneys, lungs, intestinum tenues, skins, hearts, etc. of human fetuses, and cells derived from kidneys, lungs, foreskins, placentae, lymphatic corpuscles, etc. of human adults.

Culture of the cells can be performed according to the methods which are conventionally applied to the culture of animal cells, for example, according to the method described in *Tissue Culture Methods and Applications* (P. K. Kruse and M. K. Patterson, Academic Press, 1973).

The Method (1) mentioned previously can be used for the separation and purification of the thrombin-binding substances from the culture broth.

The thrombin-binding substances (A) and (B) of this invention have calcium binding sites and change their structure by the treatment with calcium ions. Tissue culture media generally used for animal cells contain calcium ions, and therefore structurally changed thrombin-binding substances are produced in such media. When a medium not containing calcium ion is used, the calcium ion treatment is required before the culture broth is subjected to immune adsorption column chromatography. The treatment can be carried out by the addition of a calcium compound such as calcium chloride, calcium carbonate, calcium hydroxide, or the like. In general, the addition of these compounds in an amount to bring the calcium ion concentration to 2-10 mM causes thrombin-binding substances having a calcium-binding site to selectively combine with calcium and to change their structure.

Thrombin-binding substances thus prepared have the following characteristics:

(a) Molecular weight:
  Thrombin-binding substance (A):
    90,000–92,000 under reduced conditions
    55,000–58,000 under unreduced conditions
  Thrombin-binding substance (B):
    98,000–105,000 under reduced conditions
    60,000–65,000 under unreduced conditions Method of measurement: Molecular weights were measured in accordance with the Laemmli's method based on SDS-PAGE using 10% acrylamide-0.8% bisacrylamide. "Bio-Rad SDS-PAGE standard for High Molecular Substances" (trade name: product of Nippon Bio-Rad Laboratories Inc.) was used as a standard protein.

(b) Isoelectric point:
  Thrombin-binding substance (A): pH 6.0–6.8
  Thrombin-binding substance (B): pH 5.8–6.5

Method of measurement: Isoelectric points were measured according to the isoelectric point electrophoresis using Pharmacia Phast System [Plate: IEF (3–9)].

(c) Amino acid compositions:
  Amino acid compositions were determined according to the method proposed by Spacksman et al [*Anal. Chem.*, 30, 1190 (1958)] using Beckman 6300E-type Amino Acid Analyzer (trade name, manufactured by Beckman Inc.). The results are shown in Table 1. Table 1 includes, as comparative data, amino acid compositions of thrombin-binding substances reported in the following publications:

(I) *J. Biol. Chem.* 259, 12246 (1984)
(II) International Publication No. WO 87/00050
(III) Japanese Patent Laid-open No. 6219/1989
(IV) Japanese Patent Laid-open No. 301791/1988

The comparative data in Table 1 were calculated based on the data disclosed in these publications according to the same standard.

TABLE 1

| Amino acids | (A)[1] | (B)[1] | (I) | (II) | (III) Claim 1 | Claim 2 | Claim 3 | Claim 4 | Claim 5 | (IV) |
|---|---|---|---|---|---|---|---|---|---|---|
| Aspartic acid | 9.59 | 8.88 | 9.1 | 8.1 | 12.71 | 12.71 | 12.13 | 9.64 | 8.62 | 8.62 |
| Threonine | 4.45[2] | 4.80[2] | 4.4 | 6.0 | 5.08 | 4.24 | 4.78 | 4.42 | 4.31 | 4.31 |
| Serine | 5.42[2] | 5.78[2] | 7.4 | 7.9 | 3.39 | 4.66 | 6.25 | 5.82 | 5.75 | 5.75 |
| Glutamic acid | 11.29 | 9.76 | 12.5 | 6.8 | 12.71 | 12.71 | 11.40 | 10.24 | 10.23 | 10.23 |
| Proline | 8.86 | 10.21 | 5.9 | 6.5 | 9.32 | 8.90 | 10.29 | 10.04 | 9.34 | 9.34 |
| Glycine | 10.26 | 10.35 | 14.1 | 11.0 | 7.63 | 8.05 | 9.93 | 10.64 | 9.87 | 9.87 |
| Alanine | 10.88 | 10.62 | 8.8 | 8.3 | 5.93 | 7.63 | 6.99 | 10.44 | 10.77 | 10.95 |
| ½ Cystine | 8.27[4] | 8.63[4] | — | 2.5 | 15.25 | 15.25 | 13.24 | 9.24 | 8.80 | 8.80 |
| Valine | 5.54[3] | 5.71[3] | 6.3 | 8.4 | 4.24 | 4.24 | 4.78 | 5.62 | 5.90 | 5.72 |
| Methionine | 0.78 | 0.88 | 1.6 | 1.4 | 0.85 | 0.85 | 0.74 | 0.80 | 0.90 | 0.90 |
| Isoleucine | 2.84[3] | 2.65[3] | 3.4 | 5.4 | 5.08 | 3.39 | 2.94 | 2.61 | 2.87 | 2.87 |
| Leucine | 7.15 | 7.38 | 8.8 | 10.4 | 4.24 | 4.24 | 4.41 | 6.83 | 8.08 | 8.08 |
| Tyrosine | 2.25 | 2.12 | 2.8 | 2.8 | 2.54 | 2.97 | 2.57 | 2.01 | 1.97 | 1.97 |
| Phenylalanine | 3.50 | 3.53 | 2.9 | 3.2 | 5.08 | 3.39 | 2.94 | 3.21 | 2.87 | 2.87 |
| Histidine | 2.33 | 2.44 | 2.2 | 2.7 | 3.39 | 3.39 | 3.31 | 2.61 | 2.69 | 2.69 |
| Lysine | 1.12 | 1.02 | 5.0 | 3.6 | 0 | 0 | 0.37 | 0.60 | 1.44 | 1.44 |
| Tryptophan | 1.18[5] | 1.06[5] | — | — | 0 | 0 | 0 | 1.20 | 1.08 | 1.08 |
| Arginine | 4.26 | 4.19 | 4.7 | 5.1 | 2.54 | 3.39 | 2.94 | 4.02 | 4.49 | 4.49 |

[1] Measured after hydrolysis in 5.7 N hydrochloric acid at 100° C. for 24 hours.
[2] Determined by extrapolation from values measured after hydrolysis in 5.7 N hydrochloric acid at 100° C. for 24, 48 and 72 hours.
[3] Measured after hydrolysis in 5.7 N hydrochloric acid at 100° C. for 72 hours.
[4] Oxidized with performic acid and measured the produced cysteic acid.
[5] Measured after hydrolysis in 4 M methanesulfonic acid at 115° C. for 24 hours.

(d) Sugar composition:

Sugar compositions of thrombin-binding substances (A) and (B) were measured using an automatic sugar analyzer. The results are shown in Table 2.

TABLE 2

| Sugars | Sugar composition ($\mu$g/A$_{280}$)[6] (A) | (B) |
|---|---|---|
| Neutral sugars[7] | | |
| D-mannose | 24.3 | 21.1 |
| L-fucose | 15.3 | 13.6 |
| D-glucose | 27.3 | 31.1 |
| Amino sugars[8] | | |
| D-galactosamine | 6.0 | 11.3 |
| D-glucosamine | 53.5 | 47.1 |
| Sialic acid[9] | | |
| N-acetylneuraminic acid | 32.4 | 41.4 |
| Total | 158.8 | 165.6 |

[6] Proteins were determined by the UV method.
[7] Measured after hydrolysis in 2 M trifluoroacetic acid at 100° C. for 4 hours.
[8] Measured after hydrolysis in 4 M hydrochloric acid at 100° C. for 4 hours.
[9] Measured by thiobarbituric acid reaction after hydrolysis in 0.1 N sulfuric acid at 80° C. for 1 hour.

(e) Affinity:

The thrombin-binding substances have strong affinity to thrombin. 100% of both substances (A) and (B) were absorbed in a chromatographic treatment using diisopropylphosphoro-thrombin-agarose [*J. Biological Chemistry*, 245, 3059–3065 (1970)].

(f) Activity:

(1) The thrombin-binding substances bind thrombin to activate protein C.

Method of measurement: 10 $\mu$l of either one of the substances of the present invention or human thrombomodulin extracted from plancentae (5 ng/ml) dissolved in a 0.02M Tris-HCl buffer containing 0.15M sodium chloride (pH 7.5, hereinafter referred to as TBS), 30 $\mu$l of a TBS solution (1 $\mu$M) of human protein C, and 10 $\mu$l of TBS, 1% bovine serum albumin, and 5 mM calcium chloride were mixed. To this mixture 50 $\mu$l of a TBS solution of human thrombin (5 U/ml) was added and reacted at 37° C. for 30 minutes, followed by an addition of 100 $\mu$l of a TBS solution of human ATIII (50 $\mu$g/ml) and a further reaction at 37° C. for 10 minutes. To the resulting reaction mixture, 200 $\mu$l of a TBS solution containing Boc-Leu-Ser-Thr-Arg-MCM substrate (200 $\mu$M) was added to effect a reaction at 37° C. for 10 minutes. Thereafter, 600 $\mu$l of 20% acetic acid was added to terminate the reaction. The concentration of dissociated AMC was measured at an exciting light wavelength of 380 nm and an emitting light wavelength of 460 nm, whereby the concentration of activated protein C was determined. Results are shown in Table 3.

TABLE 3

| Samples (5 ng/ml) | Concentration of AMC (nmol/ml.min) |
|---|---|
| Thrombin-binding substance (A) | 13.8 |
| Thrombin-binding substance (B) | 13.6 |
| Human thrombomodulin obtained from placentae | 14.0 |

(2) Thrombin-binding substances prolong the blood clotting time.

Method of measurement: 10 $\mu$l of a TBS solution of a sample (10 $\mu$g/ml) was added to 200 $\mu$l of a 10 mM calcium chloride-containing TBS solution (0.05 U/ml) of bovine thrombin (product of Mochida Pharmaceutical Co., Ltd.). After incubation at 37° C. for 30 minutes, 200 $\mu$l of human fibrinogen was added to the solution and the clotting time was immediately measured using a fibrometer. The results are shown in Table 4.

TABLE 4

| Sample (10 $\mu$g/ml) | Clotting time (sec.) |
|---|---|
| Thrombin-binding substance (A) | 100 |
| Thrombin-binding substance (B) | 105 |
| Human thrombomodulin obtained from placentae | 120 |
| Bovine serum albumin | 78 |

(g) Stability:

Thrombin-binding substances (A) and (B) are stable to denaturing agents (sodium dodecylsulfate and urea).

Method of measurement: 45 μg of the substance was treated under the conditions shown in Table 5 at 37° C. for 60 minutes. After the treatment, the substance was diluted 100-fold with TBS to measure the residual activity. The results are shown in Table 5.

TABLE 5

| Conditions | Residual activities |
| --- | --- |
| Treatment by reduction with 1% mercaptoethanol | 0 |
| Denaturing treatment | |
| 1% SDS | 100 |
| 8 M Urea | 100 |

Since the thrombin-binding substances of this invention are high molecular weight substances with calcium-binding sites, they can be expected to exhibit more natural pharmaceutical effects than thrombin-binding substances with smaller molecular weight. In addition, such thrombin-binding substances can be industrially produced using abundantly available human urine or cells derived from human tissues as a raw material.

Other features of the invention will become apparent in the course of the following description of the exemplary embodiments which are given for illustration of the invention and are not intended to be limiting thereof.

EXAMPLES

EXAMPLE 1

600 l of fresh urine was adjusted to pH 9.0 using 6N aqueous sodium hydroxide and left at 4° C. overnight. After removing produced precipitates, 8 l of QAE-Sephadex A-50, the pH of which had been adjusted to 9.0 in advance, was added and the mixture was stirred at 4° C. for 2 hours. The resin was collected using a glass filter, washed with 10 l of 0.02M Tris-HCl buffer (pH 7.6) containing 0.05M sodium chloride, and eluted using 20 l of 0.02M Tris-HCl buffer (pH 7.6) containing 2M sodium chloride. To the eluate was added ammonium sulfate to an 80% saturation and the mixture was left at 4° C. overnight. The precipitates thus produced were collected by centrifugation, dissolved in 10 l of 0.02M Tris-HCl buffer (pH 7.6) containing 0.05M sodium chloride, and dialyzed three times against 100 l of the same buffer. To the dialyzed solution was added calcium chloride to a concentration of 5 mM and the resultant solution was subject to a diisopropylphosphoro-thrombin-agarose column. After washing with 20 l of 0.02M Tris-HCl buffer (pH 7.6) containing 0.05M sodium chloride and 5 mM calcium chloride, the column was eluted gradiently between 5 l of 0.02M Tris-HCl buffer containing 0.05M sodium chloride (minimum NaCl concentration) and 5 mM ethylenediaminetetraacetic acid and the same buffer containing 1M sodium chloride (maximum NaCl concentration) and 5 mM ethylenediaminetetraacetic acid. The eluate was fractionated in 100 ml portions. The active fractions were collected and dialyzed three times against 100 l of the same buffer containing 0.05M sodium chloride. The dialyzed solution thus obtained was subjected to a column packed with 500 ml of immunoadsorbent comprising a monoclonal antibody (TM-A91) and agarose (Japanese Patent Laid-open No. 45398/1989). After washing with 300 l of said buffer containing 1M calcium chloride, the column was eluted with 5 l of the same buffer containing 3M sodium thiocyanate and 5 mM ethylenediaminetetraacetic acid. The eluate was washed three times with 50 l of the same buffer containing 0.05M sodium chloride, dialyzed against 100 l of deionized water, and freeze-dried to obtain 10 mg of powder. The powder was dissolved in 80 ml of 0.01M Tris-HCl buffer containing 1% sodium dodecyl sulfate, 0.5% glycerol, and 0.01% bromophenol blue, and the solution was heated at 100° C. for 5 minutes. After heating, SDS-PAGE was performed according to the Laemmeli's method [*Nature*, 227, 680–685 (1970)] using 10% acrylamide-0.8% bisacrylamide to separate active fractions. Each of two fractions thus obtained was washed with water, dipped into 0.02M Tris-HCl buffer (pH 7.5) containing 1% sodium dodecyl sulfate, and left at 4° C. overnight to elute the target substances. The eluate was condensed and freeze-dried to produce 6 mg of thrombin-binding substance (A) and 2 mg of thrombin-binding substance (B).

EXAMPLE 2

1 liter of fresh urine was dialyzed three times against 5 l of 0.02M Tris-HCl buffer (pH 7.4) containing 0.05M sodium chloride. To the dialyzed solution was added calcium chloride to a concentration of nM. The dialyzed solution thus obtained was subjected to a column packed with 1 ml of immunoadsorbent of the same type as used in Example 1. After washing with 100 ml of said buffer containing 0.05M sodium chloride, 5 mM calcium chloride, and 0.05% Tween 20, and then with 100 ml of the same buffer containing 1M sodium chloride and 5 mM calcium chloride, the column was eluted using 100 ml of the same buffer containing 3M sodium thiocyanate and 5 mM ethylenediaminetetraacetic acid. The eluate was dialyzed three times against 500 ml of the same buffer containing 0.05M sodium chloride, and freeze-dried to obtain 5 μg of powder. The same SDS-PAGE as in Example 1 was performed to obtain 3 μg of thrombin-binding substance (A) and 1 μg of thrombin-binding substance (B).

EXAMPLE 3

1 ton of fresh human urine was purified with a column of immunoadsorbent comprising a monoclonal antibody (TM-A73) and QAE-Sephadex A-50, then with a diisopropylphosphoro-thrombin-agarose column, and condensed to a volume of 5 ml using Milipore Immersible CX-10. The condensate was subjected to an Ultrogel AcA 34 column (2.7×90 cm) and eluted with Tris-HCl buffer to fractionate into 2.4 ml portions. 5 mg of thrombin-binding substance (B) was obtained from the fractions 90–97 and 3 mg of thrombin-binding substance (A) was obtained from fractions 127–145.

EXAMPLE 4

$2 \times 10^5$ of kidney cells obtained from human adults were inoculated into a 75 cm$^2$ flat bottom container, to which 25 ml of MEM containing 10% of bovine fetus serum which was heat treated at 56° C. for 30 minutes. The cells were cultured using a carbon dioxide incubator at 37° C. under 5% carbon dioxide atmosphere until the cells grew to form a layer. After confirmation of the cell growth, the liquid was removed and cell surfaces were thoroughly washed with a phosphate buffer. The cells were further cultured in an MEM medium containing 20 mg/ml of proteose peptone for 7 days.

Thrombin-binding substances contained in the supernatant were measured by the ELISA method using monoclonal antibodies A-59 and A-73 and the content was found to be 10 ng/ml.

When foreskin cells of human adults were cultured in the same manner as above, the culture broth supernatant contained 40 ng/ml of thrombin-binding substances.

EXAMPLE 5

A 1 liter culture broth of kidney cells obtained from human adults and cultured in the same manner as in Example 4 was passed through a column packed with 1 ml of Sepharose (2 mg IgG/ml resin) to which monoclonal antibody A-73 was bonded. After washing with 20 ml of 0.02M Tris-HCl buffer (pH 7.4) containing 1M sodium chloride, the column was eluted with 5 ml of the same buffer containing 2M sodium thiocyanate and 5 mM EDTA and the eluate was dialyzed against 0.02M Tris-HCl buffer containing 0.1M sodium chloride.

The dialyzed solution was subjected to an Ultrogel AcA 34 column (1.7×90 cm) and eluted with 0.02M Tris-HCl (pH 7.4) buffer containing 0.15M sodium chloride at a rate of 0.1 ml/minute to fractionate into 2.4 ml portions. Fractions No. 90-95 (Fraction I) were collected together and confirmed to contain 4 μg of thrombin-binding substances by the ELISA method in the same manner as in Example 4. In the same way, fractions No. 125-135 (Fraction II) were found to contain 3 μg of thrombin-binding substances.

EXAMPLE 6

SDS-PAGE was performed according to the Laemmli's method (*Nature*, 227, 680-685) on Fractions I and II obtained in Example 5 and on the thrombin-binding substances (A) and (B) produced in Examples 1-3. The gel was transcripted onto a PVDF membrane according to the Matsudaira's method [*J. Biol. Chem.*, 262 (21), 10035-10038]. The PVDF membrane was then reacted in TBS containing 0.1% bovine serum albumin at room temperature for 2 hours. After discharging the solution, the residue was washed thoroughly with a 0.05% Tween 20-TBS, reacted in a 0.05% Tween 20-TBS 50 mM which contained monoclonal antibody A-73 labeled with horseraddish peroxidase at room temperature for 1 hour, and washed thoroughly with a 0.05% Tween 20-TBS. The liquid was discharged, and the residue was washed thoroughly with a 0.05% Tween 20-TBS and put into 50 ml of an acetic acid buffer (pH 5.0) containing 5 mg of 3-amino-9-ethylcarbazole and 25 μl of 30% hydrogen peroxide to get colored. Fraction I had a color at the same site with thrombin-binding substance (B) derived from urine and Fraction II had a color at the same site with thrombin-binding substance (A) derived from urine.

EXAMPLE 7

Each 100 μg of thrombin-binding substances (A) and (B) was subjected to Edmon degradation using a gas phase sequencer, and PTH-amino acids obtained were analyzed using a PTH analyzer. As a result, no amino acid peak was detected, evidencing that N-terminals of the thrombin-binding substances (A) and (B) were protected.

Obviously, numerous modifications and variations of the present invention are possible in light of the above teachings. It is therefore to be understood that within the scope of the appended claims, the invention may be practiced otherwise than as specifically described herein.

What is claimed is:

1. A purified thrombin-binding substance having the following characteristics:

(a) molecular weight as determined by SDS-PAGE:
       90,000-92,000 under reduced conditions
       55,000-58,000 under unreduced conditions
   (b) isoelectric point: pH 6.0-6.8
   (c) affinity: has strong affinity to thrombin
   (d) activity:
       (1) capable of promoting the thrombin catalyzed activation of protein C
       (2) prolongs clotting time; and
   (e) stability: stable to denaturing agents (sodium dodecylsulfate and urea)
   (f) amino acid composition: Aspartic acid 9.59, Threonine 4.45, Serine 5.42, Glutamic acid 11.29, Proline 8.86, Glycine 10.26, Alanine 10.88, ½ Cystine 8.27, Valine 5.54, Methionine 0.78, Isoleucine 2.84, Leucine 7.15, Tyrosine 2.25 and Phenylalanine 3.50.

2. A purified thrombin-binding substance having the following characteristics:

(a) molecular weight as determined by SDS-PAGE:
       98,000-105,000 under reduced conditions
       60,000-65,000 under unreduced conditions
   (b) isoelectric point: pH 5.8-6.5
   (c) affinity: strong affinity to thrombin
   (d) activity:
       (1) capable of promoting the thrombin catalyzed activation of protein C
       (2) prolongs clotting time; and
   (e) stability: stable to denaturing agents (sodium dodecylsulfate and urea)
   (f) amino acid composition: Aspartic acid 8.88, Threonine 4.80, Serine 5.78, Glutamic acid 9.76, Proline 10.21, Glycine 10.35, Alanine 10.62, ½ Cystine 8.63, Valine 5.71, Methionine 0.88, Isoleucine 2.65, Leucine 7.38, Tyrosine 2.12 and Phenylalanine 3.53.

3. A process for preparing the thrombin-binding substance defined in claim 1 comprising: treating human urine with calcium ion, and separating and purifying a thrombin-binding substance by immunoadsorption column chromatography using a monoclonal antibody, which is capable of recognizing structural changes in the thrombin-binding substance by calcium ion, and by a molecular weight fractionation method.

4. A process for preparing the thrombin-binding substance defined in claim 2 comprising: treating human urine with calcium ion, and separating and purifying a thrombin-binding substance by immunoadsorption column chromatography using a monoclonal antibody, which is capable of recognizing structural changes in the thrombin-binding substance by calcium ion, and by a molecular weight fractionation method.

5. A process for preparing the thrombin-binding substance defined in claim 1 comprising: culturing cells derived from human tissues, then separating and purifying the thrombin-binding substance from the culture broth using an antibody which recognizes said substance.

6. A process for preparing the thrombin-binding substance defined in claim 2 comprising: culturing cells derived from human tissues, and separating and purifying the thrombin-binding substance from the culture using an antibody which recognizes said substance.

7. The process according to claim 5 or 6, wherein said separation and purification of the thrombin-binding substance comprise subjecting said culture broth to immunoadsorption column chromatography using a monoclonal antibody, which recognizes structural changes int he thrombin-binding substance caused by calcium ion, and then to molecular weight fractionation.

* * * * *

UNITED STATES PATENT AND TRADEMARK OFFICE
CERTIFICATE OF CORRECTION

PATENT NO. : 5,043,425
DATED : AUGUST 27, 1991
INVENTOR(S) : NOBUO AOKI ET AL

It is certified that error appears in the above-identified patent and that said Letters Patent is hereby corrected as shown below:

Title Page

[30] delete "Mar. 8, 1989 [JP] Japan 1-202027", insert --Aug. 3, 1989 [JP] Japan 1-202027--.

Column 2, line 2, delete "add", insert --and--.

Column 10, line 65, delete "int he", insert --in the--.

Signed and Sealed this

Twenty-first Day of September, 1993

Attest:

BRUCE LEHMAN

*Attesting Officer*  *Commissioner of Patents and Trademarks*